(12) United States Patent
Bremer et al.

(10) Patent No.: US 10,653,569 B2
(45) Date of Patent: May 19, 2020

(54) ABSORBENT ARTICLE

(71) Applicant: SCA Hygiene Products AB, Göteborg (SE)

(72) Inventors: Christian Bremer, Göteborg (SE); Marie Kristensson, Göteborg (SE)

(73) Assignee: ESSITY HYGIENE AND HEALTH AKTIEBOLAG, Göteborg (SE)

( * ) Notice: Subject to any disclaimer, the term of this patent is extended or adjusted under 35 U.S.C. 154(b) by 0 days.

(21) Appl. No.: 15/776,945

(22) PCT Filed: Nov. 19, 2015

(86) PCT No.: PCT/SE2015/051246
§ 371 (c)(1),
(2) Date: May 17, 2018

(87) PCT Pub. No.: WO2017/086849
PCT Pub. Date: May 26, 2017

(65) Prior Publication Data

US 2018/0325747 A1 Nov. 15, 2018

(51) Int. Cl.
| | |
|---|---|
| *A61F 13/15* | (2006.01) |
| *A61F 13/20* | (2006.01) |
| *A61F 13/513* | (2006.01) |
| *A61F 13/539* | (2006.01) |
| *A61F 13/84* | (2006.01) |
| *A61F 13/511* | (2006.01) |

(52) U.S. Cl.
CPC ...... *A61F 13/51394* (2013.01); *A61F 13/513* (2013.01); *A61F 13/51104* (2013.01);
(Continued)

(58) Field of Classification Search
CPC .............. A61F 13/51104; A61F 13/513; A61F 13/51394; A61F 13/539; A61F 2013/8497; A61F 13/84; A61F 13/15731
See application file for complete search history.

(56) References Cited

U.S. PATENT DOCUMENTS

| | | | |
|---|---|---|---|
| 4,908,026 A * | 3/1990 | Sukiennik | A61F 13/53713 604/378 |
| 5,591,149 A | 1/1997 | Cree et al. | |

(Continued)

FOREIGN PATENT DOCUMENTS

| | | |
|---|---|---|
| JP | 2013-500842 A | 1/2013 |
| WO | WO-01/56526 A1 | 8/2001 |

(Continued)

OTHER PUBLICATIONS

Extended European search report dated Feb. 13, 2019 issued in European patent application No. 15908896.2.
(Continued)

*Primary Examiner* — Michele M Kidwell
(74) *Attorney, Agent, or Firm* — Faegre Drinker Biddle & Reath LLP (57) ABSTRACT

An absorbent article includes a front portion, a rear portion, a center portion located between and bordering to the front and rear portions, and a liquid pervious topsheet bonded to an underlying layer by a plurality of large and small binding points. The small binding points have a surface area in the range of 0.01-2.5 square millimeters and the large binding points have a surface area above 2.5 square millimeters. A color printing pattern is visible on a topsheet side of the absorbent article. All printed surface area of the color printing pattern onto which a disc with a diameter of 1.5 millimeters can be mapped without extending beyond a periphery of the printed surface area defines one or more continuous colored regions, and each continuous colored region within at least the center portion of the absorbent article is substantially free from large binding points.

18 Claims, 4 Drawing Sheets

(52) U.S. Cl.
CPC ............ *A61F 13/539* (2013.01); *A61F 13/84* (2013.01); *A61F 13/15731* (2013.01)

(56) References Cited

U.S. PATENT DOCUMENTS

| | | | |
|---|---|---|---|
| 7,102,054 B1* | 9/2006 | Cree | ................. A61F 13/51305<br>604/367 |
| 2008/0208154 A1* | 8/2008 | Oetjen | ..................... D04H 3/00<br>604/367 |
| 2011/0319854 A1 | 12/2011 | Suga et al. | |
| 2012/0316532 A1 | 12/2012 | McCormick | |

FOREIGN PATENT DOCUMENTS

| | | |
|---|---|---|
| WO | WO-2011/013208 A1 | 2/2011 |
| WO | WO-2011/163046 A1 | 12/2011 |

OTHER PUBLICATIONS

Russian decision to grant dated Feb. 11, 2019 issued in Russian patent application No. 2018122070 (13 pages) and its English-language translation thereof (10 pages).

Japanese Office Action dated Apr. 22, 2019 issued in Japanese patent application No. 2018526072 (4 pages) and its English-language translation thereof (4 pages).

Japanese decision to grant dated Aug. 5, 2019 issued in Japanese patent application No. 2018526072 (3 pages) and its English-language translation thereof (3 pages).

Colombian Office Action Oficio N° 9833 dated Sep. 9, 2019 issued in Colombian patent application No. NC2018/0005216 (5 pages) and its English-language translation thereof (2 pages).

Mexican Office Action No. Folio 86146 dated Oct. 14, 2019 issued in Mexican patent application No. MX/a/2018/006108 (4 pages) and its English-language translation thereof (3 pages).

\* cited by examiner

ABSORBENT ARTICLE

CROSS-REFERENCE TO PRIOR APPLICATION

This application is a § 371 National Stage Application of PCT International Application No. PCT/SE2015/051246 filed Nov. 19, 2015, which is incorporated herein in its entirety.

TECHNICAL FIELD

This disclosure relates to a disposable absorbent article having a liquid pervious topsheet bonded to an underlying layer by means of a plurality of large and small binding points and a colour printing pattern visible on a topsheet side of the absorbent article. The disposable absorbent article may typically be an incontinent shield, a sanitary napkin, a panty liner, an open-type diaper, a pant-type diaper, or the like. The disclosure is also related to a method for manufacturing such an absorbent article.

BACKGROUND

Disposable absorbent articles for receiving and retaining bodily discharges, such as urine, menstrual fluid or faces are well known in the art. Disposable absorbent articles may for example include three main layers, namely a fluid permeable topsheet, an absorbent core and a fluid impermeable backsheet. These three main layers may be mutually connected along the periphery of the absorbent article to form a single structurally interlinked product. The topsheet and the underlying sheet may additionally be connected to each other over substantial portion of the surface of the absorbent article for ensuring a satisfactory fluid transfer capacity from the topsheet to the underlying sheet. The absorbent article may further be provided with a colour print on the surface intended to face the user for indicating proper wearing of the absorbent article and enhanced visual appearance.

Document WO 2011/163046 A1 discloses a disposable absorbent article having coloured topsheet and plurality of bonded points.

While the known disposable absorbent article is satisfactory for its intended use, such absorbent article is nonetheless susceptible to improvement.

SUMMARY

It is desired to provide a disposable absorbent article and method for manufacturing such an absorbent article, where the previously mentioned problem is at least partly avoided.

The disclosure concerns an absorbent article, such as an incontinent shield, sanitary napkin, panty liner, open-type diaper, pant-type diaper, or the like, having a longitudinal direction and a transverse direction. The absorbent article including a front portion, a rear portion a centre portion located between and bordering to the front and rear portions, and a liquid pervious topsheet bonded to an underlying layer by means of a plurality of large and small binding points. The small binding points have a surface area in the range of 0.01-2.5 square millimetres and the large binding points have a surface area above 2.5 square millimetres. The absorbent article further includes a colour printing pattern that is visible on a topsheet side of the absorbent article.

All printed surface area of the colour printing pattern onto which a disc with a diameter of 1.5 millimetres can be mapped without extending beyond a periphery of the printed surface area defines one or more continuous coloured regions, and each continuous coloured region within at least the centre portion of the absorbent article is substantially free from large binding points.

It is desirable to provide at least a centre portion of the topsheet of the absorbent article with a visual appearance indicating a highly absorbent surface. This increases a user's confidence that the absorbent product has sufficient capacity to absorb any bodily discharge without leakage. One approach for indicating a highly absorbent surface on the topsheet is to use relatively large binding points for bonding the topsheet to the underlying layer. The relatively large binding points are visible to the user and give the impression that the binding points functions as through holes for enabling extra quick fluid passage from the topsheet to the underlying sheet. It is thus desirable to have relatively large binding points at least in the centre of the topsheet for giving the user improved confidence with respect to leakage security.

However, it has been observed that relatively large binding points may have negative influence on a printing pattern that is visible on a topsheet side of the absorbent article. In particular, relatively large binding points may, due to their visibility, be deemed interfering with the printing pattern, i.e. negatively influencing the visual appearance of the printing pattern. The interference may be deemed increasing with the size of the binding points as well as with the size of the coloured regions of the printing pattern. Larger coloured regions may consequently be deemed more sensible to having overlapping large binding points. Areas of the printing pattern outside of the large coloured regions, i.e. the so called discontinuous coloured region or regions of the printing pattern, may be deemed less sensible to overlapping large binding points.

Moreover, interference between large coloured regions and relatively large binding points at a centre portion of the absorbent article may be deemed more relevant than such interference at the front or rear end of the absorbent article due to the central location of the interference and closeness to the area of the absorbent article that is deemed most important for accomplishing a high leakage security.

Consequently, for the purpose of enhancing the visual appearance of the printing pattern and enabling a high perceived leakage security, it may be deemed advantageous that each continuous coloured region within at least the centre portion of the absorbent article is substantially free from large binding points.

The disclosure also concerns a corresponding method for manufacturing an absorbent article, such as an incontinent shield, sanitary napkin, panty liner, open-type diaper, pant-type diaper, or the like, having a longitudinal direction and a transverse direction, wherein the absorbent article has a front portion, a rear portion and a centre portion located between and bordering to the front and rear portions. The method includes the steps of:

printing a colour printing pattern in a web material intended to form a liquid pervious topsheet or a sheet underlying the topsheet in the absorbent article, such that the colour printing pattern is visible on a topsheet side of the finished absorbent article, and bonding the topsheet to the underlying layer by means of a plurality of large and small binding points, wherein the small binding points have a surface area in the range of 0.01-2.5 square millimetres, wherein the large binding points have a surface area above 2.5 square millimetres, and arranging the plurality of large and small binding points and the colour printing pattern such that all printed surface area of the colour printing pattern onto which a disc with a diameter of 1.5 millimetres can be mapped without extending beyond a periphery of the printed surface area defines one or more continuous coloured regions, and each continuous coloured region within at least the centre portion of the absorbent article is substantially free from large binding points.

According to an example embodiment of the absorbent article, each continuous coloured region of the absorbent article is substantially free from large binding points. Avoiding interference between relatively large binding points and large coloured regions over the entire surface of the topsheet may further enhance the perceived absorption capacity.

According to a further example embodiment of the absorbent article, all surface area of the colour printing pattern located outside of the one or more continuous coloured regions defines one or more discontinuous coloured regions, and at least 30%, specifically at least 50%, and more specifically at least 70% of the binding points located within the one or more discontinuous coloured regions are large binding points. The large binding points are generally not deemed significantly interfering with the discontinuous coloured regions because of their discontinuous nature. That is, discontinuous coloured regions nevertheless give a fragmented visual appearance, which is consequently not significantly impaired by large overlapping binding points.

According to a further example embodiment of the absorbent article, the one or more discontinuous coloured regions corresponds to all surface area of the topsheet onto which a disc with a diameter of 7 millimetres can be mapped while overlapping a printed surface area that does not form part of the one or more continuous coloured regions. Said surface area may reasonably be deemed representing discontinuous coloured regions.

According to a further example embodiment of the absorbent article, the absorbent article includes an elongated middle section extending in the longitudinal direction of the absorbent article and centred around a longitudinal centre line, and two elongated side sections extending in the longitudinal direction of the absorbent article, wherein one side section is located on each side of the middle section and extends in transverse direction from the lateral edge of the middle section to the lateral edge of the absorbent article, wherein a length of the middle section in the transverse direction is in the range of 10-60%, specifically 15-50%, and more specifically 20-40% of the maximal length of the absorbent article in the transverse direction, wherein 80-100%, specifically 90-100%, and more specifically substantially all binding points located within the central portion of the middle section are large binding points, and wherein 80-100%, specifically 90-100%, and more specifically substantially all binding points located within the central portion of the side sections are small binding points. By arranging the large binding points in a central area of the topsheet and the small binding points along the lateral sides of the topsheet a sufficient binding point density and distribution may be accomplished over a large area of the topsheet while enabling the user to perceive the large binding points in the central area as enabling enhanced absorption capacity.

According to a further example embodiment of the absorbent article, the absorbent article includes an elongated middle section extending in the longitudinal direction of the absorbent article and centred around a longitudinal centre line, and two elongated side sections extending in the longitudinal direction of the absorbent article, wherein one side section is located on each side of the middle section and extends in transverse direction from the lateral edge of the middle section to the lateral edge of the absorbent article, wherein a length of the middle section in the transverse direction is in the range of 10-60%, specifically 15-50%, and more specifically 20-40% of the maximal length of the absorbent article in the transverse direction, and wherein at least 75%, specifically at least 90%, and more specifically all surface area of the one or more continuous coloured regions within the centre portion of the absorbent article is located in any of the side sections. By locating the large coloured regions, i.e. the continuous coloured regions, in the region adjacent the lateral sides of the topsheet, large binding points may be placed in a central area of the topsheet without interfering with the large coloured regions.

According to a further example embodiment of the absorbent article, the absorbent article includes an elongated middle section extending in the longitudinal direction of the absorbent article and centred around a longitudinal centre line, and two elongated side sections extending in the longitudinal direction of the absorbent article, wherein one side section is located on each side of the middle section and extends in transverse direction from the lateral edge of the middle section to the lateral edge of the absorbent article, wherein a length of the middle section in the transverse direction is in the range of 10-60%, specifically 15-50%, and more specifically 20-40% of the maximal length of the absorbent article in the transverse direction, and wherein at least 30%, specifically at least 70%, and more specifically at least 90% of the surface area of the one or more discontinuous coloured regions within the centre portion of the absorbent article is located in the middle section. By locating the smaller coloured regions, i.e. the discontinuous coloured regions, in the central area of the topsheet, a further enhanced perception of absorption capacity may be accomplished if the printing pattern in said centre area resembles apertures or holes. A user may also deem the visual interference between the discontinuous coloured regions and large binding points as relatively low and not significantly disturbing the perceived high absorption capacity of the centre area.

According to a further example embodiment of the absorbent article, the binding points for bonding the topsheet to the underlying layer form a bonding pattern that repeats itself over the entire length of the topsheet in the longitudinal direction. As used herein, the term "repetitive binding pattern" means a binding pattern that is identical in different sections of the absorbent article, such as in at least a section of the rear portion, front portion and centre portion. This type of bonding pattern enables use of a cost-efficient roller and counter roller assembly in the manufacturing process for generating the binding points, wherein the roller may have a uniform pattern along the circumference of the roller. Moreover, the need for adapting the bonding pattering to the printing pattern may possibly be omitted.

According to a further example embodiment of the absorbent article, the binding points for bonding the topsheet to the underlying layer form a unrepetitive bonding pattern. An unrepetitive bonding pattern means a bonding pattern where for example the bonding pattern in the rear portion, front portion and central portion are different from each other. An unrepetitive bonding pattern may advantageously be positioned at a predetermined relative location to the absorbent article for accomplishing a desired visual effect, such as a predetermined relative positioning between the bonding pattering and printing pattern, or between the binding pattern and the shape and form of the absorbent article itself.

According to a further example embodiment of the absorbent article, the total surface area of the one or more continuous coloured regions amount to 3-40% of the total surface area of the centre portion of the topsheet. This range is deemed to provide a printing pattern with satisfactory visual appearance.

According to a further example embodiment of the absorbent article, the total surface area of the one or more discontinuous coloured regions amount to 20-80%, specifically 50-70% of the total surface area of the centre portion of the topsheet. This range is deemed to provide a printing pattern with satisfactory visual appearance.

According to a further example embodiment of the absorbent article, the colour printing pattern is printed on the side of the topsheet facing the underlying layer and/or on the side of the topsheet intended to face the user. Printing on the topsheet may provide a relatively high quality print due to the relatively low level of material provided between the colour of the printing pattern and an observer. Printing on the side of the topsheet facing the underlying layer may further be advantageous because the risk for smearing of the colour of the printing pattern is reduced. Topsheet printing on the side facing the user may however be advantageous in terms of perceived print quality.

According to a further example embodiment of the absorbent article, the colour printing pattern is printed on the underlying layer. This arrangement provides a relatively protected installation of the printing pattern.

According to a further example embodiment of the absorbent article, less than 30% of all binding points, specifically less than 20% of all binding points, more specifically less than 10% of all binding points, and still more specifically zero binding points, included with the one or more continuous coloured regions within the centre portion of the, or entire, absorbent article are large binding points. This arrangement is deemed to provide enhanced visual appearance of the printing pattern and high perceived leakage security.

According to a further example embodiment of the absorbent article, the material of the topsheet and the material of the underlying sheet is welded, fused and/or mechanically connected at the binding points. These types of binding technology enables cost-efficient manufacturing processes and may be used for creating the desired perceive improved liquid permeability of the topsheet.

According to a further example embodiment of the absorbent article, the binding points are formed by ultrasonic welding technique. This binding technology is advantageous due to the cost-efficient manufacturing process and high quality binding capacity.

According to a further example embodiment of the absorbent article, the total surface area of all binding points amount to 0.5-20%, specifically 3-15% of the total surface area of the centre portion of the topsheet. These ranges are deemed to provide a satisfactory contact between the topsheet and underlying sheet for adequate fluid transfer between said layers without significantly impaired fluid permeability due to excessive degree of the topsheet being covered by the binding points, as well as sufficiently large to provide the desired perceived fluid permeability due to the relatively large binding points.

According to a further example embodiment of the absorbent article, the topsheet is bonded to the underlying layer by means of a set of binding points including at least three different surface area sizes, specifically at least four different surface area sizes, and more specifically at least five different surface area sizes, wherein binding points are arranged such that the surface area size of the binding points starting from the longitudinal centre line of the absorbent article continuously or stepwise decreases towards the lateral edge of the topsheet. A continuously or stepwise reduced surface area size in the binding points from the centre line towards the lateral edge of the absorbent article may be deemed to give a visually attractive binding pattern with high perceived fluid permeability along the centreline of the absorbent article.

According to a further example embodiment of the absorbent article, the absorbent article includes an absorbent core, and the underlying layer is formed by the absorbent core or an intermediate layer positioned between the topsheet and the absorbent core.

According to a further example embodiment of the absorbent article, a maximal length of the front portion in the longitudinal direction is 15% of a maximal length the absorbent article, and a maximal length of the rear portion in the longitudinal direction is 20% of the maximal length the absorbent article. The front and rear portion according to this definition is deemed to represent portions of the absorbent article less relevant for avoiding interference between continuous colour regions and large binding points. The border lines between the front, rear and centre portions extend in the transverse direction of the absorbent article.

According to a further example embodiment of the absorbent article, each of the plurality of large and small binding points have a shape selected from the group consisting of circular, rectangular, oval, diamond, triangular and square. These types of bonding points are deemed to provide a satisfactory degree of perceived fluid permeability of the large binding points.

According to a further example embodiment of the absorbent article, the large binding points have a surface area in the range of 2.5-15 square millimetres, specifically 2.5-10 square millimetres. Surface areas of the binding points above the above-defined ranges may be deemed negatively influencing the effective fluid acquisition and transfer performance.

Further areas of applicability will become apparent from the description provided herein.

BRIEF DESCRIPTION OF DRAWINGS

In the detailed description below reference is made to the following figure, in which.

DETAILED DESCRIPTION OF EXAMPLE EMBODIMENTS

Various aspects of the disclosure will hereinafter be described in conjunction with the appended drawings to illustrate and not to limit the disclosure, wherein like designations denote like elements, and variations of the described aspects are not restricted to the specifically shown embodiments, but are applicable on other variations of the disclosure.

Figure 1:
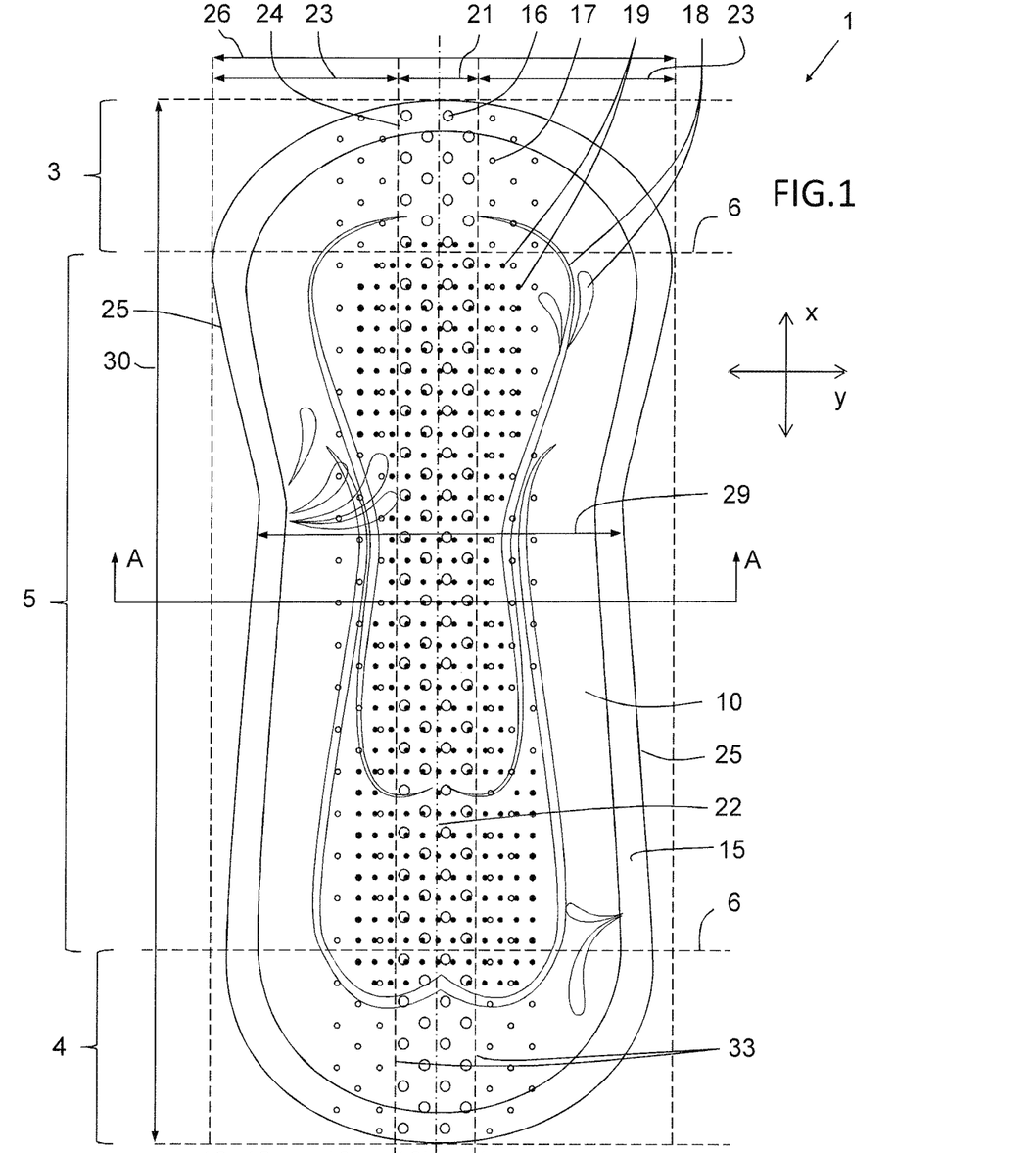
FIG. 1 shows a top view of an example embodiment of the absorbent article according to the disclosure.

With reference to FIG. 1 of the drawings, an example embodiment of an absorbent article 1 according to the disclosure of is schematically illustrated from a side facing the topsheet 10 of the absorbent article 1. The example embodiment schematically shows a wing-less sanitary napkin type absorbent article 1 having a longitudinal direction x and a transverse direction y. The absorbent article 1 further includes a front portion 3, a rear portion 4 a centre portion 5 located between and bordering to the front and rear portions 3, 4. The border lines 6 between said portions 3, 4, 5 are parallel and extend in the transverse direction y.

In the example embodiment of FIG. 1, the maximal length of the front portion 3 in the longitudinal direction x is about 15% of a maximal length 30 the absorbent article in the longitudinal direction x. Moreover, a maximal length of the rear portion 4 in the longitudinal direction x is about 20% of the maximal length 30 of the absorbent article in the longitudinal direction x.

The disclosed example absorbent article 1 embodiment has an elongated shape along a longitudinal direction x, wherein the width 29 in a centre portion 5 of the absorbent article 1 is smaller than a maximal width of the absorbent article 1 at said front and rear portions 3, 4.

The disclosed example absorbent article 1 embodiment further has an asymmetric shape about an axis extending in the transverse direction y because the location of the most narrow portion of the absorbent article 1 in the transverse direction y is located closer to a front end of the absorbent article than a rear end of the absorbent article. Alternatively, the absorbent article may have a mirror symmetry about an axis extending in the transverse direction y.

Figures 2A, 2B:
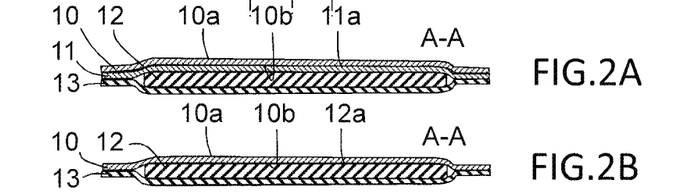
FIG. 2A shows an example cross-sectional view along cut A-A of FIG. 1.
FIG. 2B shows an alternative cross-sectional view along cut A-A of FIG. 1.

An example embodiment of a cross-sectional view along section A-A of FIG. 1 is schematically shown in FIG. 2A. The absorbent article 1 according to this specific example embodiment includes a liquid pervious topsheet 10 bonded to an underlying acquisition or distribution layer 11, a liquid impermeable backsheet 13, and an absorbent core 12 sandwiched between the acquisition or distribution layer 11 and the liquid impermeable backsheet 13. The absorbent core 12 may be adhesively attached to the acquisition or distribution layer 11. However, many variations in terms of structure of the absorbent article 1 are possibly within the scope of the claims. For example, the underlying layer may be another type of layer, or one or more additional layers may be provided in the absorbent article. Furthermore, with reference to FIG. 2B, the topsheet 10 may be bonded directly to the absorbent core 12, or to another layer that is not an acquisition or distribution layer or an absorbent core. Moreover, the absorbent core 12 may include two or more layers of absorbent materials that jointly form the absorbent core 12.

The example sanitary napkin shown in FIG. 1 is a wing-less sanitary napkin-type absorbent article 1 that is intended to be adhesively attached to an underwear of a user, for example by means of adhesive that is provided of the outer side of a backsheet 13 for fastening the absorbent article to said underwear. However, the disclosure is equally applicable to wing-type sanitary napkin absorbent articles, where laterally protruding wings at the centre portion 5 of the absorbent article 1 are intended to be folded around the edge of the underwear of a user for fastening the absorbent article 1 to said underwear. Moreover, the underlying inventive concept of the present disclosure may equally well be implemented in an absorbent article 1 designed and configured to function as a incontinent shield, a panty liner, a sanitary napkin, an open-type diaper, a pant-type diaper, or the like.

The liquid permeable topsheet 10 can include a nonwoven material, e.g., spunbonded, meltblown, carded, hydroentangled, wetlaid, etc. which can be composed of natural fibres, such as woodpulp or cotton fibres, synthetic fibres, such as polyester, polyethylene, polypropylene, viscose, etc. or from a mixture thereof The topsheet 10 material may further be composed of tow fibres, porous foams, apertured plastic films etc. The materials suited as topsheet materials should be soft and non-irritating to the skin and be readily penetrated by body fluid, e g urine or menstrual fluid, and display low rewetting properties. The topsheet may include weldable fibres for enabling bonding to the underlying sheet by means of welding, such as ultrasonic welding.

The acquisition or distribution layer 11, if such a layer is used in absorbent article 1, may comprise a material suitable for bonding to the topsheet 10. For example, if welding technology is used for bonding the topsheet 10 to the acquisition or distribution layer 11 the material of the acquisition or distribution layer 11 should include at least partly weldable fibres. For example, the weldable fibres may polyethylene fibres coated with a layer of polypropylene. The acquisition or distribution layer 11 may further include pure polyethylene fibres. In a specific example less than 30% of the fibres in the acquisition or distribution layer 11 are polyethylene fibres and more than 70% of the fibres are welding fibres consisting of polyethylene fibres coated with polypropylene.

The absorbent core 12 may include any conventional material suitable for absorbing discharged bodily wastes, such as cellulosic fluff pulp, tissue layers, highly absorbent polymers (superabsorbents), absorbent foam materials including hydrogel-foam material, absorbent nonwoven materials or the like. Similar to above, if welding technology is used for bonding the topsheet 10 directly to the absorbent core 12 the material of the absorbent core 12 should include at least partly weldable fibres.

The liquid impermeable backsheet 13 may include a thin plastic film, e.g., a polyethylene or polypropylene film, a nonwoven material coated with a liquid impervious material, a hydrophobic nonwoven material which resists liquid penetration or laminates of plastic films and nonwoven materials. The backsheet material may be breathable so as to allow vapour to escape from the absorbent core, while still preventing liquids from passing through the backsheet material.

The topsheet 10 and backsheet 13 may be connected to each other along a peripheral bonding zone 15 extending along a periphery of the absorbent article. The bond in the peripheral boding zone 15 may for example be realised by means of adhesive bonding, gluing or welding by heat or ultrasonic bonding. The topsheet 10 and/or the backsheet 13 may further be attached to the absorbent core 12 by any method known in the art, such as adhesive, heat-bonding etc.

For enabling a satisfactory fluid transfer performance from the topsheet 10 to the underlying sheet and for the purpose of providing the user with a low sense of wetness, a relatively close contact between the topsheet 10 and underlying layer is desirable over a substantial area of the topsheet 10 located inside of the peripheral bonding zone 15. This relatively close contact is in the example embodiment of FIG. 1 accomplished by means of a plurality of large and small binding points 16, 17 distributed over the area of the topsheet 10 inside of the peripheral bonding zone 15.

Too many binding points 16, 17 have a negative effect on fluid transfer performance and sensed wetness due to the low or inexistent fluid transfer performance at the area of each binding point 16, 17 itself. It is thus desirable to have a reasonable amount of binding points 16, 17 more or less equally distributed over the area of the topsheet 10.

It is furthermore desirable to have relatively large binding points 16 at least in a region of absorbent article 1 intended for first receiving body fluid because the relatively large binding points 17 may be more visible to user, wherein the user may perceive the visible large binding points 17 as an indication of high absorption capacity due to their perceived appearance as through holes through the topsheet 10.

The binding points may for example be realised by means of welding, fusing and/or mechanically connecting the material of the topsheet and the material of the underlying sheet at the binding points. Specifically, the binding points may be formed by ultrasonic welding technique. The plurality of large and small binding points may have a shape selected from the group consisting of circular, rectangular, oval, diamond, triangular and square.

In the example embodiment of FIG. 1 the binding points used for bonding the topsheet to the underlying layer form a bonding pattern that repeats itself over the entire length of the topsheet in the longitudinal direction. However, the binding points may alternatively form an unrepetitive bonding pattern, such as for example a bonding pattern that is shaped according to a non-uniform overall outer shape of the absorbent article, and/or bonding pattern that is shaped according to a non-uniform printing pattern of the absorbent article.

The total surface area of all binding points amounts to about 4% of the total surface area of the centre portion 5 of the topsheet in the example embodiment of FIG. 1. However, the total surface area of all binding points may alternatively amount to about 0.5-20% of the total surface area of the centre portion of the topsheet 10, specifically to about 3-15% of the total surface area of the centre portion 5 of the topsheet.

The example embodiment of the sanitary napkin schematically illustrated in FIG. 1 additionally includes a colour printing pattern that is visible on a topsheet side of the absorbent article 1. The colour printing pattern schematically illustrated in FIG. 1 includes a decorative colour print in form of printed leaf-shaped elements 18 and elongated elements 18 resembling stems or the like. The stems are located adjacent and at least partly substantially parallel with the lateral edges 25 of the absorbent article 1. This arrangement is used for illustrating and/or strengthening the perceived form, shape and/or suitable orientation of the absorbent article during use, as well as enhancing the visual appearance of the absorbent article 1.

Moreover, the colour printing pattern of the absorbent article 1 of FIG. 1 additionally includes a plurality of small colour printed elements 19 that are provided for further strengthening the perceived fluid permeability of the topsheet 10 for improved leakage security. The fluid permeability is deemed strengthened due to the visual similarity between the plurality of small colour printed elements 19 and apertures through the topsheet 10. The plurality of small colour printed elements 19 may for example have a shape selected from the group consisting of circular, rectangular, oval, diamond, triangular and square.

Since the absorbent article 1 includes both a plurality of binding points 16, 17 and a colour printing pattern having various printed elements 18, 19 visible on a topsheet side of the absorbent article 1 undesirable interference between the printing pattern and the binding points 16, 17 may occur, at least where relatively large binding point overlaps a continuous colour region of the printing pattern. It may therefore be desirable to use relatively small binding points 17, in addition the previously mentioned relatively large binding points 16, because the relatively small binding points 17 are generally less visible to the user and consequently less likely to induce an undesirable interference between the printing pattern and the binding points 16, 17.

The liquid pervious sheet 10 according to the disclosure is therefore bonded to the underlying layer by means of a plurality of large binding points 16 and small binding points 17. The size of the surface area of the binding points 16, 17 used for bonding the topsheet 10 to the underlying sheet consequently varies over the area of the topsheet 10. In the example embodiment shown in FIG. 1, the small binding points 17 have a surface area of about 1 square millimetre, and the large binding points 16 have a surface area of about 4 square millimetres. However, the small binding points 17 may alternatively have a surface area in the range of 0.01-2.5 square millimetres, specifically 0.1-2.0 square millimetres, and more specifically 0.25-1.5 square millimetres, and the large binding points 16 may alternatively have a surface area above 2.5 square millimetres. The large binding points 16 may have a surface area in the range of 2.5-15 square millimetres, specifically 2.5-10 square millimetres.

A continuous colour region refers to a colour printed region having a certain continuous extension, contrary to a plurality of small coloured elements. In detail, a continuous colour region is herein defined as a printed surface area of the colour printing pattern onto which a disc with a diameter of 1.5 millimetres can be mapped without extending beyond a periphery of the printed surface area. The various continuous colour regions 20 of the example embodiment absorbent article of FIG. 1 are clearly indicated as hatched regions in FIG. 3. These colour regions 20 represent areas having relatively large continuous colourings.

Figures 3, 4:
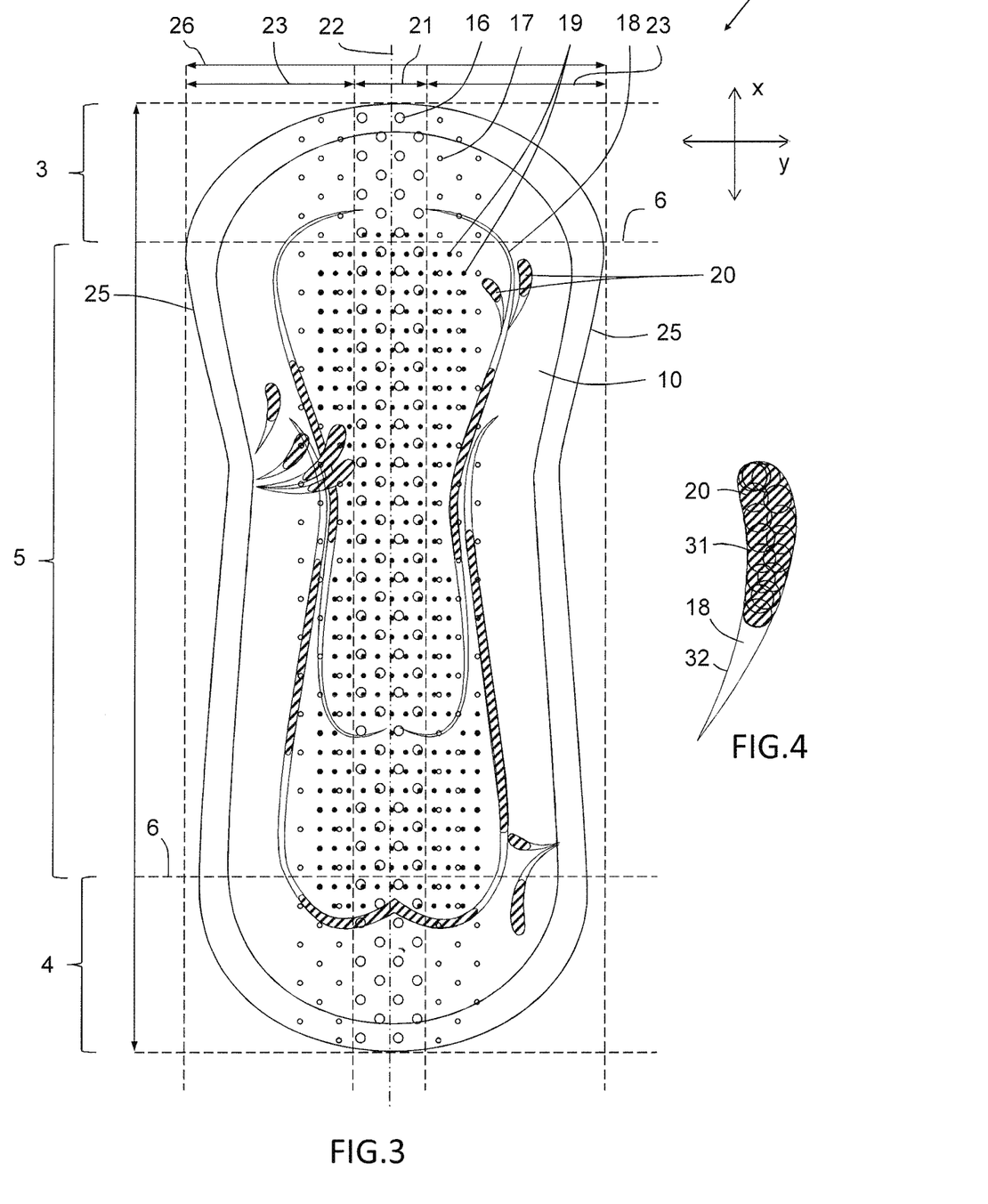
FIG. 3 shows an example of the continuous colour regions of the absorbent article of FIG. 1.
FIG. 4 shows an example of a printed surface area having a continuous colour region.

An enlarged example decorative colour print in form of printed leaf-shaped element 18 is illustrated in FIG. 4 for the purpose of showing the definition of a continuous colour region 20. A plurality of discs with a diameter of 1.5 millimetres are mapped on the printed element 18 without extending beyond a periphery 32 of the printed surface area. Only the portion of the printed surface area 18 onto which said disc can be mapped without extending beyond a periphery of the printed surface area is deemed belonging to the continuous colour region 20, which is identified by means of a hatched area on FIG. 4.

For accomplishing the desired effect of relatively large binding points 16 over at least a portion of the area of the topsheet 10 in combination with a printing pattern that includes at least one continuous colour region 20, and still avoiding undesired perceived interference between large binding points 16 and the printing pattern, the location of the large binding points 16 and continuous colour regions 20 are arranged such that each continuous coloured region 20 within at least the centre portion 5 of the absorbent article 10 is substantially free from large binding points 16.

In the example embodiment of FIG. 1 zero binding points 16, 17, are included with the one or more continuous coloured regions within the centre portion of the absorbent article. However, substantially free from large binding points 16 herein includes example embodiments having less than 30% of all binding points 16, 17, specifically less than 20% of all binding points 16, 17, more specifically less than 10% of all binding points 16, 17 included with the one or more continuous coloured regions within the centre portion of the absorbent article, or within the entire absorbent article, are large binding points 16. All binding points 16, 17 herein refers to those binding points that are located inside of the peripheral bonding zone 15 extending along a periphery of the absorbent article 1.

The centre portion 5 of the absorbent article 10 may often be deemed more important with respect to absorption capacity and therefore avoiding or reducing interference between large binding points 16 and continuous colour regions 20 is most relevant in this portion of the absorbent article 1. However, according to an alternative embodiment, each continuous coloured region 20 of the absorbent article 1 may be substantially free from large binding points 16 for further enhanced perceived absorption capacity.

Colour printed surface area onto which a disc with a diameter of 1.5 millimetres cannot be mapped without extending beyond a periphery of the printed surface area is consequently not part of a continuous colour region. Instead, all surface area of the colour printing pattern located outside of the one or more continuous coloured regions defines one or more discontinuous coloured regions.

Since the relatively large binding points 16 are deemed attractive for the purpose of providing perceived high absorption capacity, but results in unsatisfactory visual interference with continuous colour regions, the relatively large binding points are, in particular embodiments, located outside of the continuous colour regions. The large binding points may for example instead be located within a discontinuous coloured region. In particular, at least 30%, specifically at least 50%, and more specifically at least 70% of the binding points located within the one or more discontinuous coloured regions are large binding points.

Figure 5:
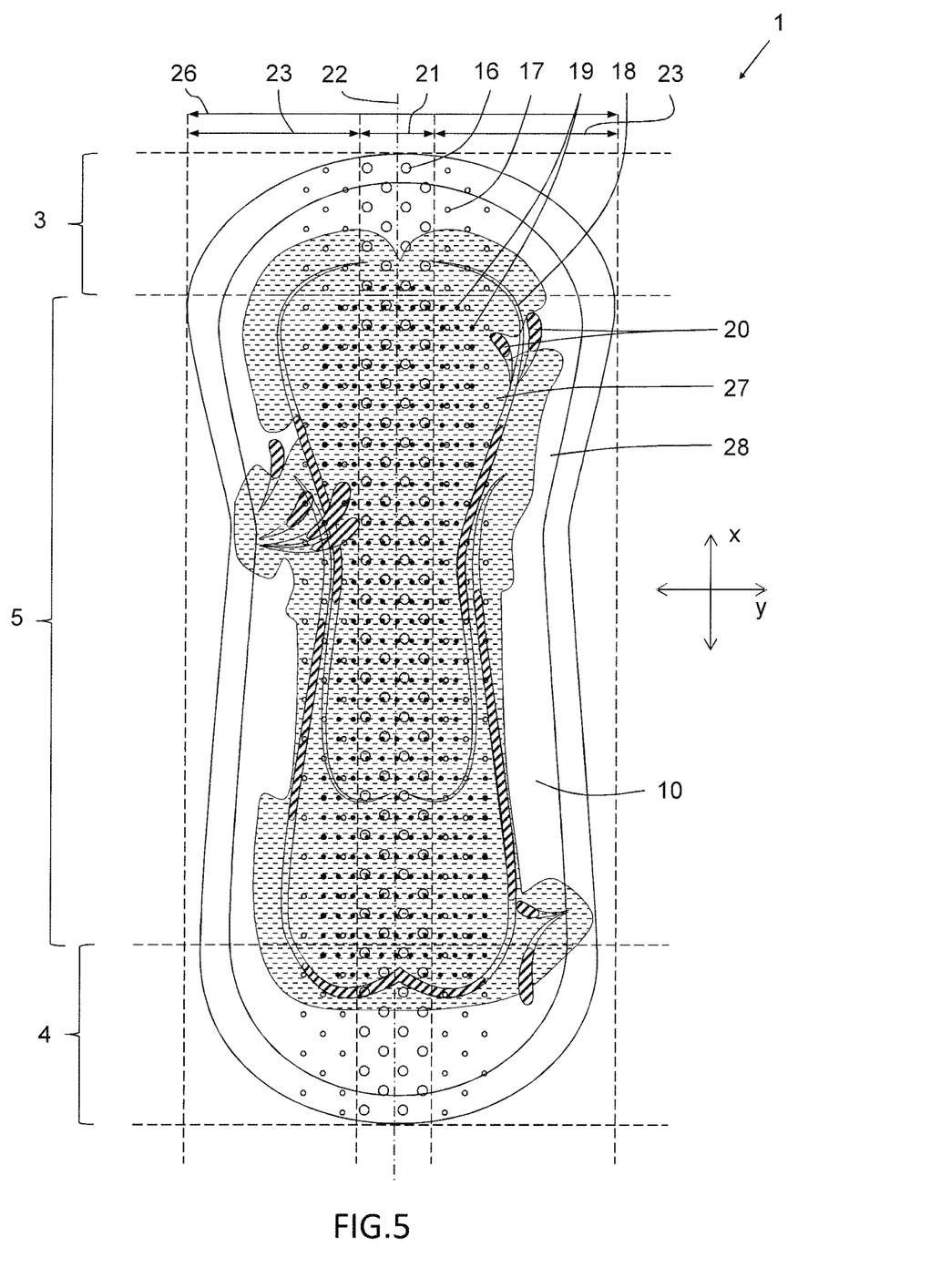
FIG. 5 shows an example of a discontinuous colour region of the absorbent article of FIG. 1.

A discontinuous coloured region corresponds essentially to a region that is associated with the area of the colour printing pattern but not part of any of the continuous colour regions. In detail, discontinuous coloured region herein refers to a surface area of the topsheet onto which a disc with a diameter of 7 millimetres can be mapped while overlapping a printed surface area that does not form part of the one or more continuous coloured regions. An example illustration of the area of the discontinuous colour region 27 is shown in FIG. 5 together with the area of the continuous colour regions 20. Other sizes of the disc different from 7 millimetres may be used for defining the discontinuous colour region 27, such as for example 6 millimetres, 5 millimetres or 4 millimetres. The total surface area of the topsheet 10 consists of the continuous colour region(s) 20, the discontinuous colour region(s) 27 and the remaining unprinted region 28 of the topsheet 10.

The colour print may for example be realised by means of analogue or digital printing technology. Analog printing technology herein refers to the use of printing plates or rolls that are coated with colour liquid and subsequently pressed on a surface to be printed, such that the surface to be printed is provided with a colour printing pattern. Digital printing technology typically refers to inkjet printing where ink is transferred onto the substrate to create the desired image, electrophotography printing where toner is attracted to a charged image and then developed, or laser printing. Where digital printing is used the colour printing pattern may be accomplished by printing a large number of small colour dots very close to each other. The resolution of the colour printing pattern may be defined in terms of dots per inch (DPI). A disc with a diameter of 1.5 millimetres mapped onto a printed surface area is not deemed extending beyond a periphery of the printed surface area merely because the printed surface area has a low resolution, when the printed surface area extends both in the longitudinal direction x and transverse direction and when the resolution is at least 50 DPI, specifically at least 100 DPI, both in the longitudinal and transverse direction x, y.

Alternatively, or in combination with above, the location of the large binding points may be separated from the location of the continuous colour regions by means of splitting up the surface of the topsheet 10 into various sections and assigning each section with either large biding points to continuous colour regions. For example, the absorbent article may include an elongated middle section 21 extending in the longitudinal direction x of the absorbent article 1 and centred around a longitudinal centre line 22, and two elongated side sections 23 extending in the longitudinal direction x of the absorbent article 1, wherein one side section 23 is located on each side of the middle section 21. The side sections 23 extend in transverse direction y from the lateral edge 24 of the middle section to the lateral edge 25 of the absorbent article 1.

In the example embodiment of FIG. 1, the length of the middle section 21 in the transverse direction y is about 20% of the maximal length 26 of the absorbent article 1 in the transverse direction y. However, the length of the middle section 21 in the transverse direction y may alternatively be in the range of 10-60%, specifically 15-50%, and more specifically 20-40% of the maximal length 26 of the absorbent article 1 in the transverse direction y.

Alternatively, or in combination with above, the separation of the large binding points 16 and continuous colour regions 20 may be implemented by locating at least 75%, specifically at least 90%, and more specifically all surface area of the one or more continuous coloured regions 20 within the centre portion 5 of the absorbent article 1 in any of the side sections 23. In the example embodiment of FIG. 3 all surface area of the one or more continuous coloured regions 20 within the centre portion 5 of the absorbent article 1 is located in the side sections 23. By locating at least a substantial part of the continuous colour regions 20 in the side sections 23 the middle section 21 is relatively free from continuous colour regions 20, such that the large binding points 16 can be located in the middle section 21 with low or no risk for interference.

Alternatively, or in combination with above, the separation of the large binding points 16 and continuous colour regions 20 may be implemented by locating 80-100%, specifically 90-100%, and more specifically substantially all large binding points 16 within a central portion 5 of the middle section 21, and locating 80-100%, specifically 90-100%, and more specifically substantially all small binding points 17 within the central portion 5 of the side sections 23. In the example embodiment of FIG. 3 all binding points within the central portion 5 of the side sections 23 are small binding points 17 and all binding points within the central portion 5 of the middle section 21 are large binding points 16. Similar to above, by locating at least a substantial part of the large binding points 16 in the middle section 21 the side sections 23 are relatively free from large binding points 16, such that the continuous colour regions 20 can be located in the side section 23 with low or no risk for interference. The small binding points 17 also located in the side sections 23 does not induce any significant interference with the continuous colour regions when arranged overlappingly.

Still more alternatively, or in combination with above, the separation of the large binding points 16 and continuous colour regions 20 may be implemented by locating at least 30%, specifically at least 70%, and more specifically at least 90% of the surface area of the one or more discontinuous coloured regions within the centre portion of the absorbent article in the middle section 21. In the example embodiment of FIG. 5 about 30% of the surface area of the discontinuous coloured region 27 within the centre portion 5 of the absorbent article is located in the middle section 21. In an embodiment, the large binding points 16 are located in the middle section 21 for the purpose of accomplishing a high perceived absorption capacity. Arranging also a significant part of the discontinuous colour region 27 with the middle section 21 may be desirable because the large binding points 16 are not deemed inducing any significant interference with the discontinuous colour region 27 when arranged overlappingly.

The example embodiment of the absorbent article in FIG. 3 has relatively low amount continuous colour regions, the total surface area of the continuous coloured regions 20 in FIG. 3 amount to about 5% of the total surface area of the centre portion 5 of the topsheet 10. The total surface area of the continuous coloured regions 20 is FIG. 3 amounts to the accumulated surface of the hatched area. The total surface area of the centre portion 5 of the topsheet 10 amount to all surface surrounded by the lateral edges 25 of the absorbent article 1 and the border lines 6 between the front portion 3, rear portion 4 and centre portion 5, respectively.

The total surface area of the one or more discontinuous coloured regions typically amount to 20-80%, specifically 50-70% of the total surface area of the centre portion of the topsheet. In the example embodiment of FIG. 5, the total surface area of the discontinuous coloured region 27 amounts to about 75% of the total surface area of the centre portion of the topsheet.

With reference to FIG. 2A, the colour printing pattern may for example be printed on the side 10b of the topsheet 10 facing the underlying layer, which here is represented by an acquisition or distribution layer 11. Alternatively, or in combination with above, the colour printing pattern may for example be printed on the side 10a of the topsheet 10 intended to face the user. Still more alternatively, or in combination with above, the colour printing pattern may be printed on the acquisition or distribution layer 11, such as the side 11a of the acquisition or distribution layer 11 facing the user. With reference to FIG. 2B, if the underlying layer is the absorbent core 12, the colour printing pattern may alternatively be printed on the side 12a of the absorbent core intended to face the user.

Figure 6:
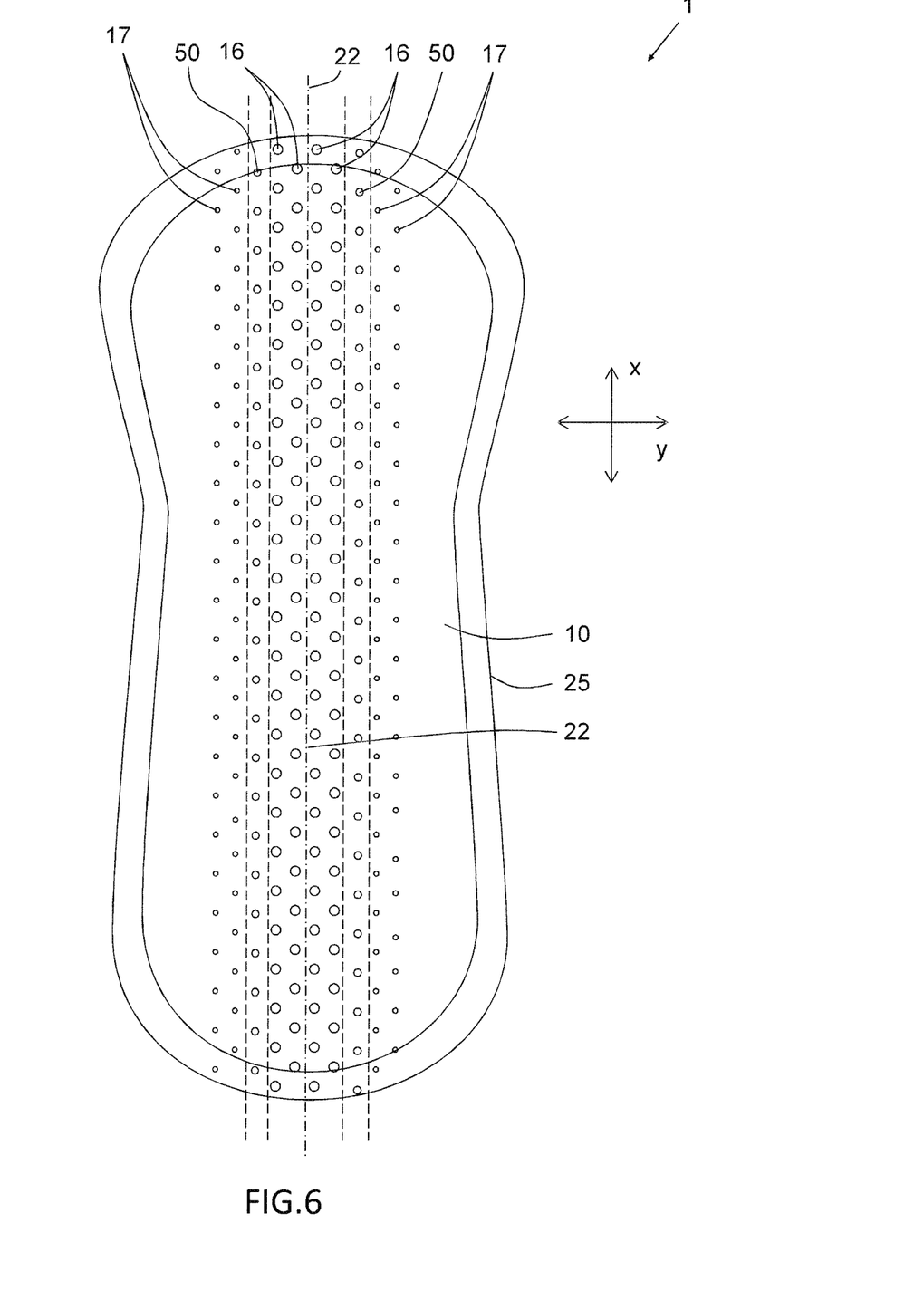
FIG. 6 shows an alternative embodiment of the bonding pattern of the absorbent article.

In the previously disclosed example embodiments of the absorbent article, two different binding point sizes were shown, large binding points 16 located in the middle section 21 small binding points located in the side sections 23. However, the topsheet 10 may alternatively be bonded to the underlying layer by means of a set of binding points including at least three different surface area sizes. Such an example embodiment is schematically shown in FIG. 6 with the colour printing pattern hidden for providing a more understandable disclosure. In FIG. 6 four longitudinal lines of large binding points 16 are provided centred around the longitudinal centre line 22. A line of intermediate sized binding points 50 having a smaller surface area that the large binding points 16 are arranged on each lateral outer side of the large binding points 16. Finally, two longitudinal lines of small binding points 17 are arranged on each lateral outer side of the intermediate binding points 50. The binding points 16, 50, 17 are thus arranged such that the surface area size of the binding points 16, 50, 17 starting from the longitudinal centre line 22 of the absorbent article 1 stepwise decreases towards the lateral edge 25 of the topsheet 10.

When the absorbent article is a sanitary napkin, panty liner or similar type of product having no elastic threads or bands integrated into the absorbent article, all measurements in length, surface areas and diameters etc. herein are intended to be performed in natural state of the absorbent article. However, in case the absorbent article includes elastic threads or bands, such as typically used in pant-type incontinence products, baby open diapers, standing gathers, or the like, all measurements in length, surface areas and diameters etc. herein are intended to be performed in an extended state of the absorbent article. As used herein, the term "extended state" of the absorbent article is defined as a state in which the absorbent article has been extended in all four direction to such an extent that all the elastic materials contained therein, such as the elastic web material, the waist elastics, the leg elastics, are extended to such an extent that they will not gather any part of the product, but the entire absorbent article is substantially flat and in an un-gathered state. The article is extended only to such an extent that this flat condition is reached.

It will be appreciated that the above description is merely exemplary in nature and is not intended to limit the present disclosure, its application or uses. While specific examples have been described in the specification and illustrated in the drawings, it will be understood by those of ordinary skill in the art that various changes may be made and equivalents may be substituted for elements thereof without departing from the scope of the present invention as defined in the claims. the mixing and matching of features, elements and/or functions between various examples is expressly contemplated herein so that one of ordinary skill in the art would appreciate from this disclosure that features, elements and/or functions of one example may be incorporated into another example as appropriate, unless described otherwise, above. Moreover, many modifications may be made to adapt a particular situation or material to the teachings of the present disclosure without departing from the essential scope thereof Therefore, it is intended that the present invention not be limited to the particular examples illustrated by the drawings and described in the description, but that the scope of the present invention will include any embodiments falling within the appended claims.

Reference signs mentioned in the claims should not be seen as limiting the extent of the matter protected by the claims, and their sole function is to make claims easier to understand.

The invention claimed is:

1. An absorbent article having a longitudinal direction and a transverse direction, the absorbent article comprising:
    a front portion;
    a rear portion;
    a center portion located between and bordering to the front and rear portions, wherein a maximal length of the front portion in the longitudinal direction is 15% of a maximal length the absorbent article in the longitudinal direction, and a maximal length of the rear portion in the longitudinal direction is 20% of the maximal length the absorbent article in the longitudinal direction;
    an elongated middle section extending in the longitudinal direction of the absorbent article and centered around a longitudinal center line, and
    two elongated side sections extending in the longitudinal direction of the absorbent article, wherein one side section is located on each side of the middle section and extends in transverse direction from a lateral edge of the middle section to a lateral edge of the absorbent article, wherein a length of the middle section in the transverse direction is in the range of 10-60% of the maximal length of the absorbent article in the transverse direction;
a liquid pervious topsheet bonded to an underlying layer by a plurality of large and small binding points, wherein the small binding points have a surface area in the range of 0.01-2.5 square millimeters, and wherein the large binding points have a surface area above 2.5 square millimeters; and
a discontinuous printed layer forming a color printing pattern on a surface of the topsheet or the underlying layer, wherein the color printing pattern is visible on a topsheet side of the absorbent article,
wherein all printed surface area of the color printing pattern, onto which a disc with a diameter of 1.5 millimeters can be mapped without extending beyond a periphery of the printed surface area, defines one or more continuous colored regions, and each continuous colored region within at least the center portion of the absorbent article is substantially free from large binding points,
wherein at least 75% of the one or more continuous colored regions within the center portion of the absorbent article is located in any of the side sections,
wherein at least 30% of the surface area of the one or more discontinuous colored regions within the center portion of the absorbent article is located in the middle section,
wherein at least 30% of the binding points located within the one or more discontinuous colored regions are large binding points,
wherein the total surface area of the one or more continuous colored regions amount to 3-40% of the total surface area of the center portion of the topsheet, and
wherein the total surface area of the one or more discontinuous colored regions amount to 20-80% of the total surface area of the center portion of the topsheet.

2. The absorbent article according to claim 1, wherein each continuous colored region of the absorbent article is substantially free from large binding points.

3. The absorbent article according to claim 1, wherein all surface area of the color printing pattern located outside of the one or more continuous colored regions defines one or more discontinuous colored regions.

4. The absorbent article according to claim 3, wherein the one or more discontinuous colored regions corresponds to all surface area of the topsheet onto which a disc with a diameter of 7 millimeters can be mapped while overlapping a printed surface area that does not form part of the one or more continuous colored regions.

5. The absorbent article according to claim 1,
wherein 80-100% of the binding points located within the central portion of the middle section are large binding points, and
wherein 80-100% of the binding points located within the central portion of the side sections are small binding points.

6. The absorbent article according to claim 1, wherein the binding points for bonding the topsheet to the underlying layer form a bonding pattern that repeats itself over the entire length of the topsheet in the longitudinal direction.

7. The absorbent article according to claim 1, wherein the binding points for bonding the topsheet to the underlying layer form a unrepetitive bonding pattern.

8. The absorbent article according to claim 1, wherein the color printing pattern is printed on the side of the topsheet facing the underlying layer and/or on the side of the topsheet intended to face the user.

9. The absorbent article according to claim 1, wherein the color printing pattern is printed on the underlying layer.

10. The absorbent article according to claim 1, wherein less than 30% of all binding points included with the one or more continuous colored regions within the absorbent article are large binding points.

11. The absorbent article according to claim 1, wherein material of the topsheet and material of the underlying sheet is welded, fused and/or mechanically connected at the binding points.

12. The absorbent article according to claim 1, wherein the binding points are formed by ultrasonic welding.

13. The absorbent article according to claim 1, wherein the total surface area of all binding points amount to 0.5-20% of the total surface area of the center portion of the topsheet.

14. The absorbent article according to claim 1, wherein the topsheet is bonded to the underlying layer by a set of the binding points including at least three different surface area sizes, wherein the binding points are arranged such that the surface area size of the binding points starting from a longitudinal center line of the absorbent article continuously or stepwise decreases towards a lateral edge of the topsheet.

15. The absorbent article according to claim 1, further comprising: an absorbent core, and the underlying layer is formed by the absorbent core or an intermediate layer positioned between the topsheet and absorbent core.

16. The absorbent article according to claim 1, wherein each of the plurality of large and small binding points has a shape selected from the group consisting of circular, rectangular, oval, diamond, triangular, and square.

17. The absorbent article according to claim 1, wherein the large binding points has a surface area in the range of 2.5-15 square millimeters.

18. A method for manufacturing an absorbent article having a longitudinal direction, a transverse direction, a front portion, a rear portion, and a center portion located between and bordering to the front and rear portions, wherein a maximal length of the front portion in the longitudinal direction is 15% of a maximal length the absorbent article in the longitudinal direction, and a maximal length of the rear portion in the longitudinal direction is 20% of the maximal length the absorbent article in the longitudinal direction, an elongated middle section extending in the longitudinal direction of the absorbent article and centered around a longitudinal center line, and two elongated side sections extending in the longitudinal direction of the absorbent article, wherein one side section is located on each side of the middle section and extends in transverse direction from a lateral edge of the middle section to a lateral edge of the absorbent article, wherein a length of the middle section in the transverse direction is in the range of 10-60% of the maximal length of the absorbent article in the transverse direction, comprising:
printing a discontinuous printed layer forming a color printing pattern on a surface of a liquid pervious topsheet or a sheet underlying the topsheet in the absorbent article, such that the color printing pattern is visible on a topsheet side of the finished absorbent article;
bonding the topsheet to the underlying layer by a plurality of large and small binding points, the small binding points having a surface area in the range of 0.01-2.5 square millimeters, the large binding points having a surface area above 2.5 square millimeters,
wherein the plurality of large and small binding points and the colour printing pattern are arranged during printing and bonding such that all printed surface area of the color printing pattern onto which a disc with a diameter of 1.5 millimeters can be mapped without extending beyond a periphery of the printed surface area defines one or more continuous colored regions, and each continuous colored region within at least the center portion of the absorbent article is substantially free from large binding points, wherein at least 75% of the one or more continuous colored regions within the center portion of the absorbent article is located in any of the side sections, wherein at least 30% of the surface area of the one or more discontinuous colored regions within the center portion of the absorbent article is located in the middle section, wherein at least 30% of the binding points located within the one or more discontinuous colored regions are large binding points, wherein the total surface area of the one or more continuous colored regions amount to 3-40% of the total surface area of the center portion of the topsheet, and wherein the total surface area of the one or more discontinuous colored regions amount to 20-80% of the total surface area of the center portion of the topsheet.

* * * * *